(12) United States Patent
Rubie et al.

(10) Patent No.: US 10,874,529 B2
(45) Date of Patent: Dec. 29, 2020

(54) APPARATUS AND METHOD FOR A PROSTHETIC FOOT COVER

(71) Applicant: Fillauer Composites LLC, Salt Lake City, UT (US)

(72) Inventors: Eric Rubie, Salt Lake City, UT (US); Phillip Thompson, Salt Lake City, UT (US)

(73) Assignee: Fillauer Composites LLC, Salt Lake City, UT (US)

( * ) Notice: Subject to any disclaimer, the term of this patent is extended or adjusted under 35 U.S.C. 154(b) by 62 days.

(21) Appl. No.: 15/998,761

(22) Filed: Aug. 16, 2018

(65) Prior Publication Data

US 2019/0060090 A1 Feb. 28, 2019

Related U.S. Application Data

(60) Provisional application No. 62/547,181, filed on Aug. 18, 2017.

(51) Int. Cl.
*A61F 2/66* (2006.01)
*A61F 2/50* (2006.01)

(52) U.S. Cl.
CPC .......... *A61F 2/66* (2013.01); *A61F 2002/5001* (2013.01); *A61F 2002/5023* (2013.01); *A61F 2002/5075* (2013.01); *A61F 2002/5083* (2013.01); *A61F 2002/6614* (2013.01); *A61F 2002/6621* (2013.01); *A61F 2002/6664* (2013.01)

(58) Field of Classification Search
CPC ........................... A61F 2/66; A61F 2002/5001
See application file for complete search history.

(56) References Cited

U.S. PATENT DOCUMENTS

| 8,128,709 | B2 * | 3/2012 | Thorhallsdottir | ......... A61F 2/66 623/53 |
|---|---|---|---|---|
| 2013/0218297 | A1 * | 8/2013 | Nordman, Jr. | ............ A61F 2/66 623/53 |

\* cited by examiner

*Primary Examiner* — Bruce E Snow
(74) *Attorney, Agent, or Firm* — Chambliss, Bahner & Stophel, P.C.

(57) ABSTRACT

A prosthetic foot cover for a prosthetic foot having a sagittal plane and a plantar surface including a first cover component having a first internal cavity and being adapted to receive and cover a first portion of the prosthetic foot, a second cover component having a second internal cavity and being adapted to receive and cover a second portion of the prosthetic foot, and a means for detachably attaching the first cover component and the second cover component to the prosthetic foot. The first internal cavity has a first internal cavity contacting surface that directly contacts the first portion of the prosthetic foot, and the second internal cavity has a second internal cavity contacting surface that directly contacts the second portion of the prosthetic foot. A method for installing the prosthetic foot cover on the prosthetic foot.

22 Claims, 16 Drawing Sheets

APPARATUS AND METHOD FOR A PROSTHETIC FOOT COVER

CROSS-REFERENCES TO RELATED APPLICATIONS/PATENTS

This application relates back to and claims the benefit of priority from U.S. Provisional Application for Patent Ser. No. 62/547,181 titled "Prosthetic Foot Cover" and filed on Aug. 18, 2017.

FIELD OF THE INVENTION

The present invention relates generally to apparatuses and methods for prosthetic foot covers, and particularly to apparatuses and methods for multi-component prosthetic foot covers.

BACKGROUND AND DESCRIPTION OF THE PRIOR ART

It is known to use apparatuses and methods to cover a prosthetic foot. Conventional apparatuses and methods, however, suffer from one or more disadvantages. For example, conventional foot covers are one-piece shells that do not provide any functional improvement to prosthetic feet. More particularly, conventional foot covers restrict the transverse movement and multi-axial performance of prosthetic feet. Conventional foot covers are also difficult to install and remove. Further, conventional foot covers have undesirably large internal cavities. As a result, they allow prosthetic feet to move relative to the foot covers, collect fluids and debris, and do not provide support along the entire plantar surface of the prosthetic feet or a smooth rollover. Still further, the undesirably large internal cavity of conventional foot covers is typically filled with a substance that inhibits the movement of the prosthetic feet. In addition, conventional foot covers are not sufficiently durable and have undesirably short lifespans. Conventional foot covers also do not have a variable stiffness from a higher stiffness near the prosthetic foot interface to a softer stiffness at the shoe or ground interface. Conventional foot covers also do not provide the user with sufficient feedback, unimpeded flexion, and energy return because their internal cavities are not matched to interface with the foot and the covers are made from inferior materials such as silicone, EVA foam, and the like which tend to have a dampening effect that decreases the fidelity of the ground reaction forces experienced by the user.

It would-be desirable, therefore, if an apparatus and method for a prosthetic foot cover could be provided that would improve the functionality of prosthetic feet. More particularly, it would be desirable if such an apparatus and method for a prosthetic foot cover could be provided that would not restrict transverse movement of prosthetic feet and would improve multi-axial performance of prosthetic feet. It would be further desirable if such an apparatus and method for a foot cover could be provided that would be easy to install and remove. It would be still further desirable if such an apparatus and method for a foot cover could be provided that-would not have an undesirably large internal cavity. More particularly, it would be desirable if such an apparatus and method for a foot cover could be provided that would not move relative to prosthetic feet, would not collect fluids or debris, and would provide support along the entire plantar surface of the prosthetic feet and a smooth rollover. It would be still further desirable if such an apparatus and method for a foot cover could be provided that would not require a filler substance or inhibit the movement of the prosthetic feet. In addition, it would be desirable if such an apparatus and method for a foot cover could be provided that would be durable and have a long lifespan. Furthermore, it would be desirable if such an apparatus and method for a foot cover could be provided that would have a variable stiffness from a higher stiffness near the prosthetic foot interface to a softer stiffness at the shoe or ground interface so as to allow transverse movement and support lateral loads on the foot prosthesis more continuously and reduce internal stresses so as to add to the durability and life of the foot cover and the foot. It would also be desirable if such an apparatus and method for a foot cover could be provided that would provide the user with sufficient feedback, unimpeded flexion, and energy return and not tend to have a dampening effect that decreases the fidelity of the ground reaction forces experienced by the user.

ADVANTAGES OF THE PREFERRED EMBODIMENTS OF THE INVENTION

Accordingly, it is an advantage of the preferred embodiments of the invention claimed herein to provide an apparatus and method for a foot cover that improves the functionality of prosthetic feet. It is also an advantage of the preferred embodiments of the invention claimed herein to provide an apparatus and method for a foot cover that does not restrict the transverse movement of prosthetic feet and improves the multi-axial performance of prosthetic feet. It is another advantage of the preferred embodiments of the invention claimed herein to provide an apparatus and method for a foot cover that is easily installed and removed. It is still another advantage of the preferred embodiments of the invention claimed herein to provide an apparatus and method for a foot cover that does not have a large internal cavity. It is yet another advantage of the preferred embodiments of the invention claimed herein to provide an apparatus and method for a foot cover that does not move relative to prosthetic feet or collect fluid and debris and does provide support over the entire plantar surface of prosthetic feet and a smooth rollover. Further, it is an advantage of the preferred embodiments of the invention claimed herein to provide an apparatus and method for a foot cover that does not require filler substance or inhibit the movement of prosthetic feet. Still further, it is an advantage of the preferred embodiments of the invention claimed herein to provide an apparatus and method for a foot cover that is durable and has a long lifespan. It is yet another advantage of the preferred embodiments of the invention claimed herein to provide an apparatus and method for a foot cover that has a variable stiffness from a higher stiffness near the prosthetic foot interface to a softer stiffness at the shoe or ground interface so as to allow transverse movement and support lateral loads on the foot prosthesis more continuously and reduce internal stresses so as to add to the durability and life of the foot cover and the foot. It is also an advantage of the preferred embodiments of the invention claimed herein to provide the user with sufficient feedback, unimpeded flexion, and energy return and not tend to have a dampening effect that decreases the fidelity of the ground reaction forces experienced by the user.

Additional advantages of the preferred embodiments of the invention will become apparent from an examination of the drawings and the ensuing description.

EXPLANATION OF THE TECHNICAL TERMS

As used herein, the term "prosthetic foot" means any lower limb device, mechanism, assembly, or combination thereof that functions as an artificial substitute or replacement for a-user's lower limb. The term "prosthetic foot" includes without limitation articulated prostheses, non-articulated prostheses, solid ankle cushioned heel (SACH) prostheses, elastic (flexible) keel prostheses, single-axis prostheses, multi-axis prostheses, dynamic-response prostheses, split-toe prostheses, microprocessor prostheses, myoelectric prostheses, and robotic prostheses.

SUMMARY OF THE INVENTION

The apparatus of the invention comprises a prosthetic foot cover for a prosthetic foot having a sagittal plane. The preferred prosthetic foot cover comprises a first cover component having a first internal cavity and being adapted to receive and cover a first portion of the prosthetic foot, a second cover component having a second internal cavity and being adapted to receive and cover a second portion of the prosthetic foot, and a means for detachably attaching the first cover component and the second cover component to the prosthetic foot. In the preferred prosthetic foot cover, the first internal cavity has a first internal cavity contacting surface that directly contacts the first portion of the prosthetic foot, and the second internal cavity has a second internal cavity contacting surface that directly contacts the second portion of the prosthetic foot.

The method of the invention comprises a method for covering a prosthetic foot having a sagittal plane. The preferred method comprises providing a prosthetic foot cover. The preferred prosthetic foot cover comprises a first receive and cover component having a first internal cavity and being adapted to cover a first portion of the prosthetic foot, a second cover component having a second internal cavity and being adapted to receive and cover a second portion of the prosthetic foot, and a means for detachably attaching the first cover component and the second-cover component to the prosthetic foot. In the preferred prosthetic foot cover, the first internal cavity has a first internal cavity contacting surface that directly contacts the first portion of the prosthetic foot, and the second internal cavity has a second internal cavity contacting surface that directly contacts the second portion of the prosthetic foot. The preferred method further comprises installing the prosthetic foot cover on the prosthetic foot.

BRIEF DESCRIPTION OF THE DRAWINGS

The presently preferred embodiments of the invention are illustrated in the accompanying drawings, in which like reference numerals represent like parts throughout, and in which.

DESCRIPTION OF THE PREFERRED EMBODIMENTS OF THE INVENTION

Figure 1:
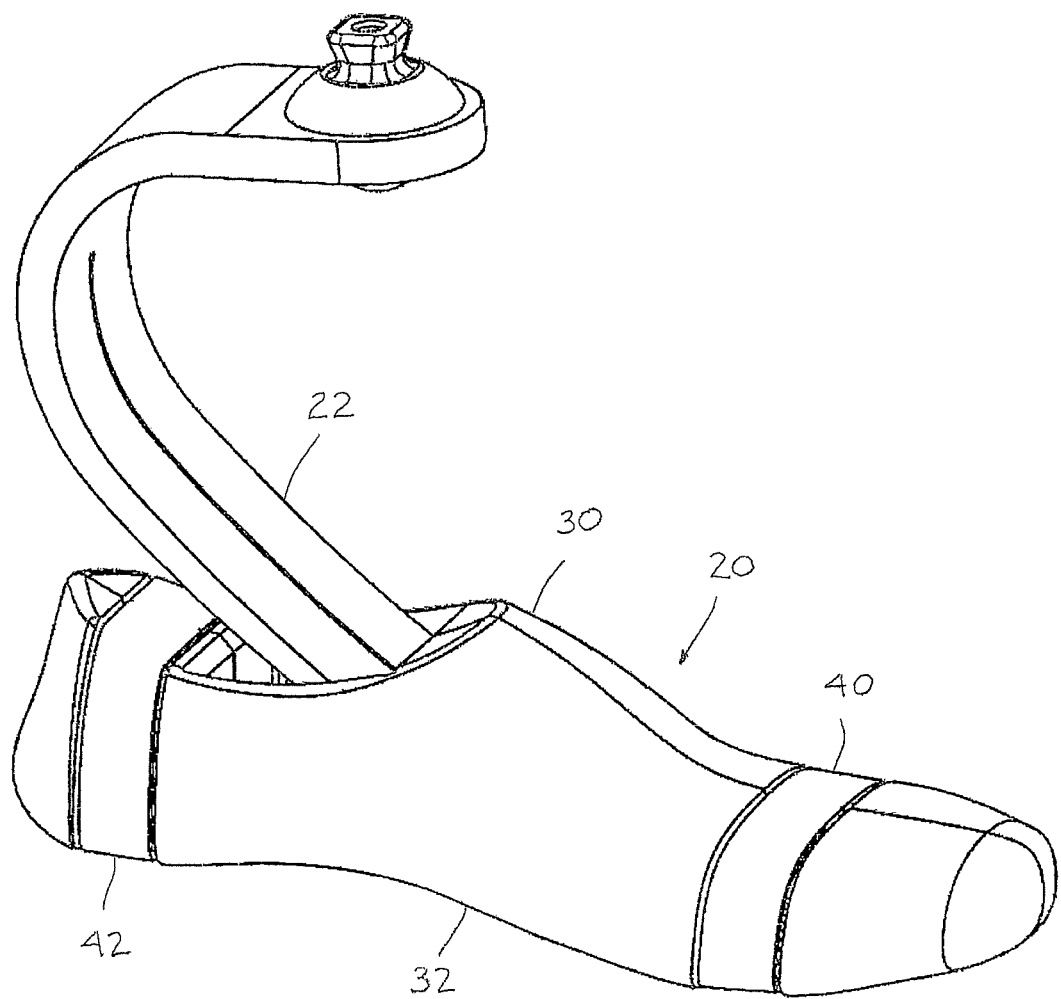
FIG. 1 is a front perspective view of the preferred embodiment of the prosthetic foot cover in accordance with the present invention shown on an exemplary prosthetic foot.

Referring now to the drawings, the preferred embodiments of the prosthetic foot cover in accordance with the present invention is illustrated by FIGS. 1 through 16. As shown in FIGS. 1-16, the preferred prosthetic foot covers are multi-component assemblies adapted to be easily installed on and removed from a variety of different-shaped and different-sized prosthetic feet such that the internal cavity contacting surfaces of the foot covers do not move relative to the foot. The preferred prosthetic foot covers are also adapted to provide support to a prosthetic foot along the entire plantar surface of the prosthetic foot and prevent the collection of fluids and debris. Further, the preferred foot covers do not restrict the movement of the prosthetic foot and improve the performance and durability of the prosthetic foot. Still further, the preferred foot covers provide the user with sufficient feedback, unimpeded flexion, and energy return, and they do not tend to have a dampening effect that decreases the fidelity of the ground reaction forces experienced by the user.

Referring now to FIG. 1, a front perspective view of the preferred embodiment of the prosthetic foot cover in accordance with the present invention shown on an exemplary prosthetic foot is illustrated. As shown in FIG. 1, the preferred prosthetic foot cover is designated generally by reference numeral 20. Preferred prosthetic foot cover 20 is illustrated with exemplary prosthetic foot 22 having sagittal plane 24 (see FIGS. 7 and 8). Preferred prosthetic foot cover 20 comprises first cover component 30, second cover component 32, and a-means for detachably attaching the first cover component and the second cover component to exemplary prosthetic foot 22 such as compression bands 40 and 42. Preferably, first cover component 30 and second cover component 32 are detachably attached along the sagittal plane of the prosthetic foot and around the prosthetic foot. Preferred first cover component 30 and preferred second cover component 32 comprise a polyurethane such as Volkollan® premium performance polyurethane (Desmodur® 15 base, polyester polyol, and one or more special chain extenders or cross-linking agents). It is also contemplated within the scope of the invention, however, that preferred first cover component 30 and preferred second cover component 32 may comprise ethylene-vinyl acetate and/or a thermoplastic elastomer. It is further contemplated within the scope of the invention that the means for detachably attaching the first cover component and the second cover component may comprise a hook and loop fastener, a clip, a threaded fastener, a groove, a hole, an elastomeric material, a compression sock, or any other suitable device, mechanism, assembly, or combination thereof. While FIG. 1 illustrates the preferred configuration and arrangement of prosthetic foot cover 20, it is contemplated within the scope of the invention that the prosthetic foot cover may be of any suitable configuration and arrangement.

Figure 2:
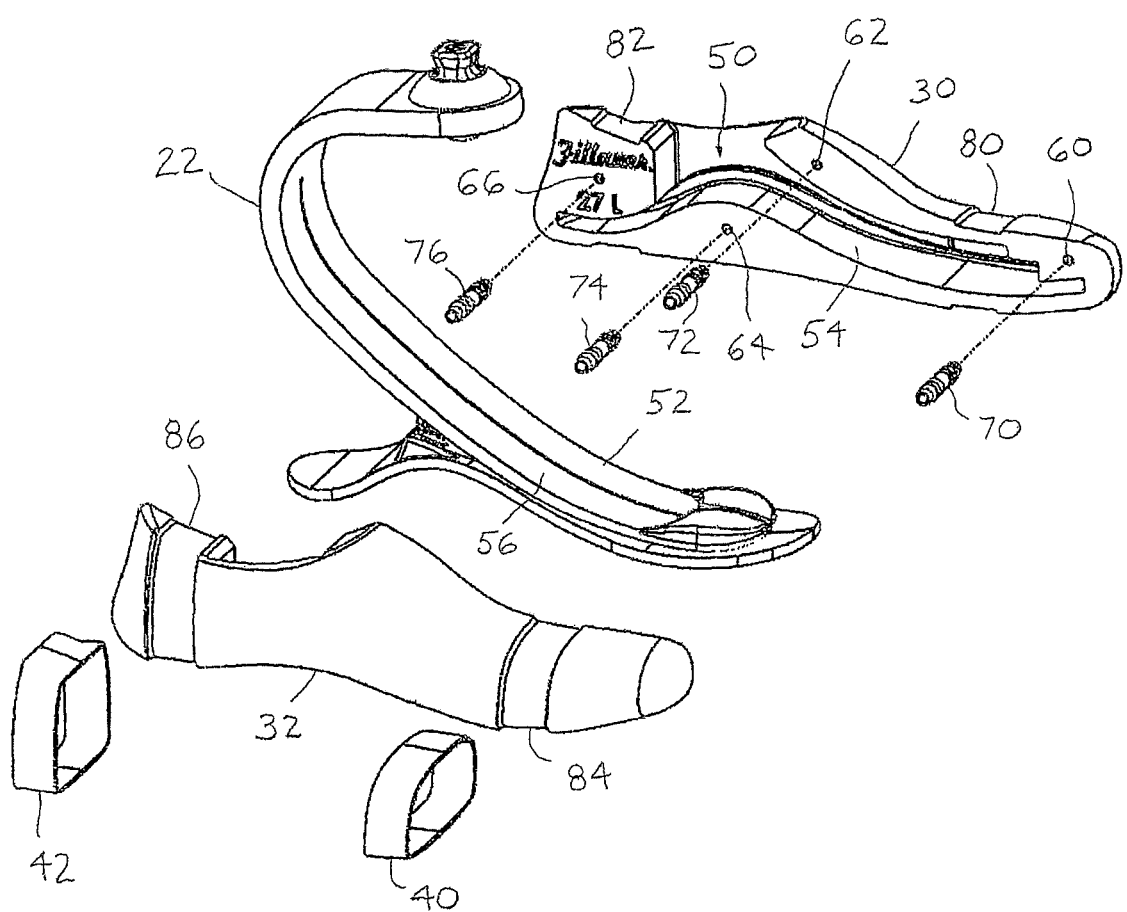
FIG. 2 is a front perspective exploded view of the preferred prosthetic foot cover and the exemplary prosthetic foot illustrated in FIG. 1.

Referring now to FIG. 2, a front perspective exploded view of preferred prosthetic foot cover 20 and exemplary prosthetic foot 22 is illustrated. As shown in FIG. 2, preferred first cover component 30 has first internal cavity 50 that is adapted to receive and cover first portion 52 of prosthetic foot 22. More particularly, preferred first internal cavity 50 has first internal cavity contacting surface 54 that directly contacts the first portion of the prosthetic foot such that the first internal cavity contacting surface of first cover component 30 does not move relative to first portion 52 of prosthetic foot 22. Preferred prosthetic foot cover 20 also comprises second cover component 32 which is adapted to receive and cover second portion 56 of prosthetic foot 22. Preferred prosthetic foot cover 20 further comprises a means for detachably attaching the first cover component and the second cover component to prosthetic foot 22 such as compression bands 40 and 42. In addition, preferred prosthetic foot cover 20 comprises a plurality of first cover holes 60, 62, 64, and 66 which are adapted to receive connectors 70, 72, 74, and 76. Preferred holes 60, 62, 64, and 66 are sized to be slightly smaller than preferred connectors 70, 72, 74, and 76 in order to achieve a snug fit. Preferred connectors 70, 72, 74, and 76 are barbed plastic hose connectors, but it is contemplated within the scope of the invention that the connectors may be any suitable device, mechanism, assembly, or combination thereof adapted to detachably attach the first cover component and the second cover component. Still further, preferred prosthetic foot cover 20 comprises a pair of first cover grooves 80 and 82 and a pair of second cover grooves 84 and 86 which are adapted to receive and retain compression bands 40 and 42.

While FIG. 2 illustrates the preferred configuration and arrangement of the first internal cavity, the first internal cavity contacting surface, the first cover holes, the hose connectors, the first cover grooves, and the second cover grooves, it is contemplated within the scope of the invention that the first internal cavity, the first internal cavity contacting surface, the first cover holes, the hose connectors, the first cover grooves, and the second cover grooves may be of any suitable configuration and arrangement. It is also contemplated within the scope of the invention that there may be more or fewer than four (4) first cover holes and more or fewer than (4) hose connectors. More particularly, it is contemplated within the scope of the invention that there are no first cover holes and no hose connectors. In addition, it is contemplated within the scope of the invention that there are more or fewer than two (2) first cover grooves and more or fewer than two (2) second cover grooves. It is also contemplated within the scope of the invention that there are no first cover grooves and no second cover grooves.

Figure 3:
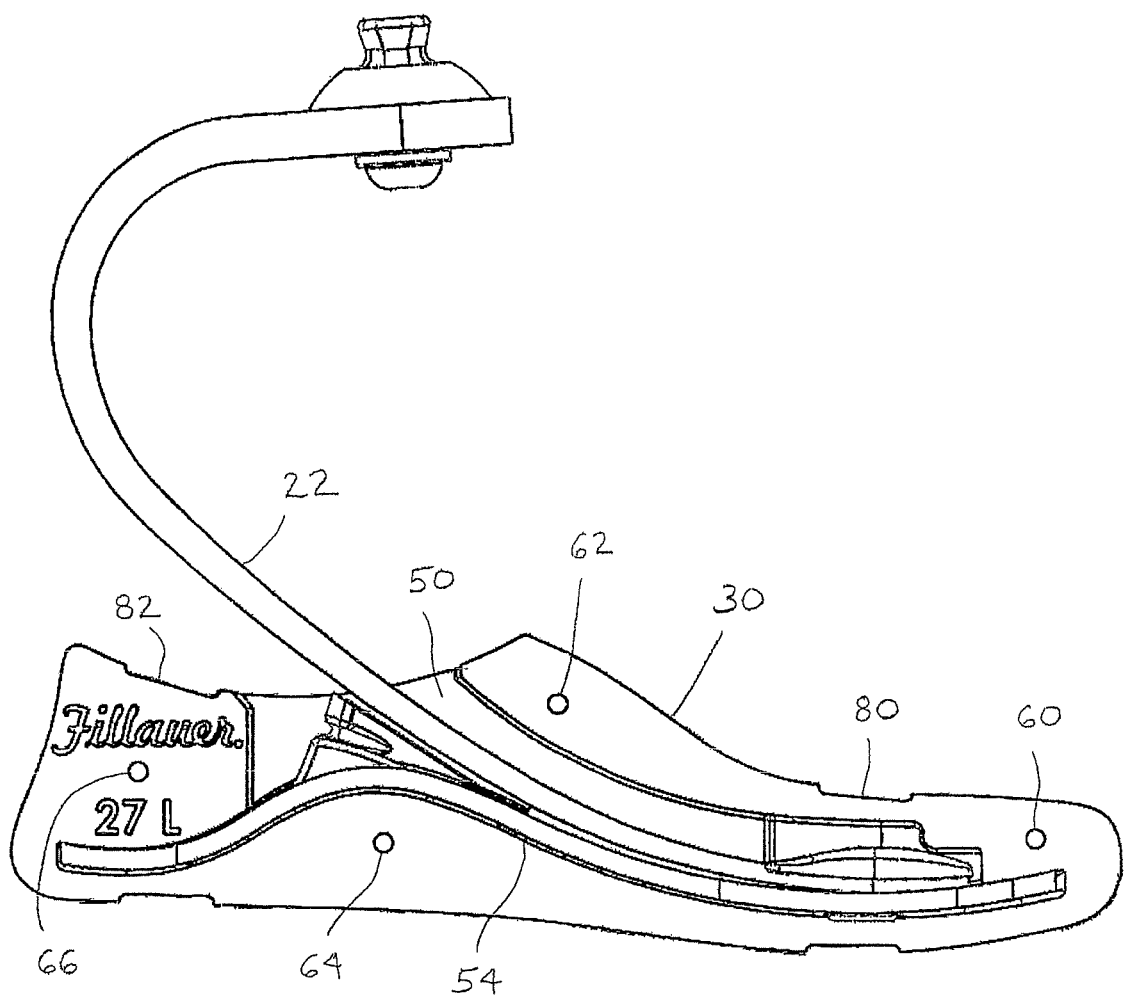
FIG. 3 is a right side partial sectional view of the preferred left side prosthetic foot cover and the exemplary prosthetic foot illustrated in FIGS. 1-2.

Referring now to FIG. 3, a right side partial sectional view of preferred prosthetic foot cover 20 and exemplary prosthetic foot 22 is illustrated. As shown in FIG. 3, preferred prosthetic foot cover 20 comprises first cover component 30 having first internal cavity 50 and first internal cavity contacting surface 54 which contacts and supports substantially the entire plantar surface of prosthetic foot 22. Preferred prosthetic foot cover 20 also comprises first cover holes 60, 62, 64, and 66 and first cover grooves 80 and 82. Furthermore, first cover component 30 (and/or second cover component 32) may be still at first internal cavity contacting surface 54 and then gradually less stiff in a direction perpendicular to the contacting surface so as to evenly distribute transverse loads, allow transverse movement, and reduce internal stresses to increase durability. In addition, bottom surface 88 has a curvature that allows a smooth foot rollover.

Figure 4:
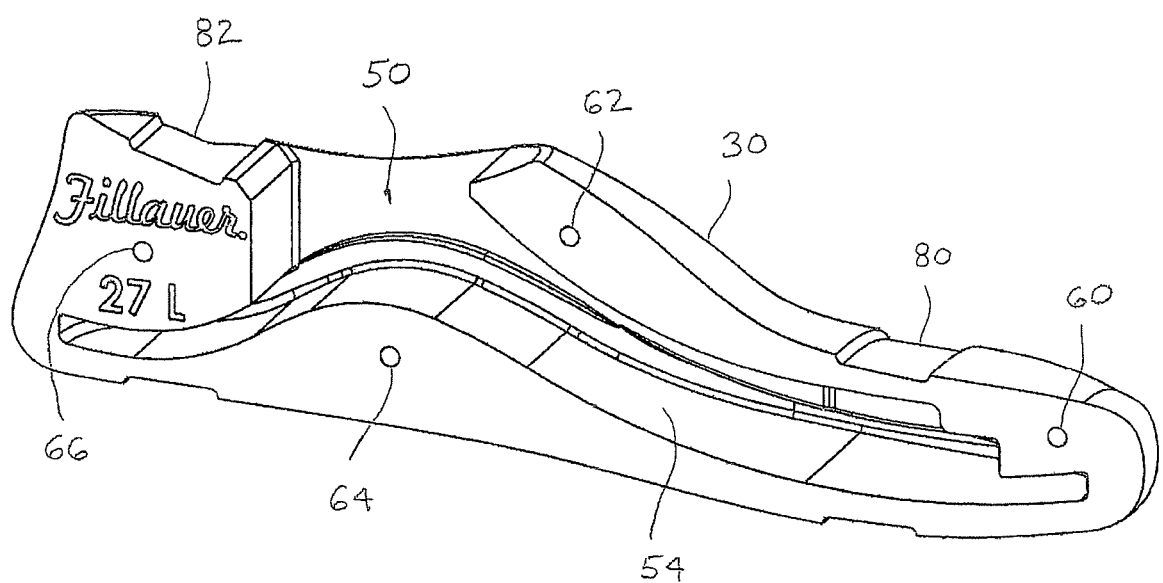
FIG. 4 is a front perspective view of the preferred left side prosthetic foot cover illustrated in FIGS. 1-3.

Referring now to FIG. 4, a front perspective view of preferred first cover component 30 is illustrated. As shown in FIG. 4, preferred first cover component 30 comprises first internal cavity 50 and first internal cavity contacting surface 54 which contacts and supports substantially the entire plantar surface of exemplary prosthetic foot 22. Preferred prosthetic foot cover 20 also comprises first cover holes 60, 62, 64, and 66 and first cover grooves 80 and 82.

Figure 5:
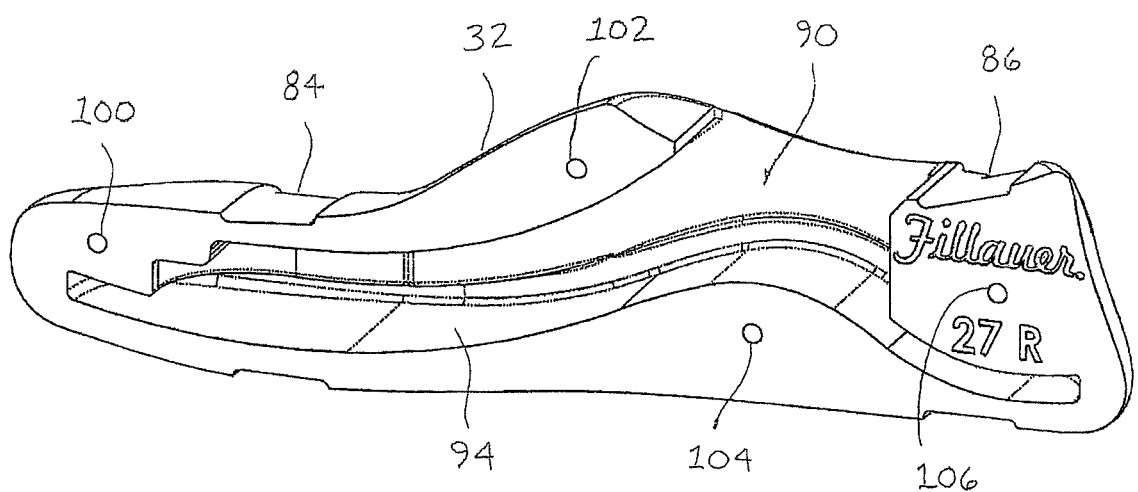
FIG. 5 is a rear perspective view of the preferred right side prosthetic foot cover illustrated in FIGS. 1-2.

Referring now to FIG. 5, a rear perspective view of preferred second cover component 32 is illustrated. As shown in FIG. 5, preferred second cover component 32 comprises second cover grooves 84 and 86, second internal cavity 90, and second internal cavity contacting surface 94 which directly contacts second portion 56 of exemplary prosthetic foot 22. Preferably, second-internal cavity contact surface 94 contacts and supports substantially the entire plantar surface of exemplary prosthetic foot 22 and does not move relative to second portion 56 of the exemplary prosthetic foot. Preferred prosthetic foot cover 20 also comprises second cover holes 100, 102, 104, and 106. Preferred holes 100, 102, 104, and 106 are sized to be slightly smaller than preferred connectors 70, 72, 74, and 76 in order to achieve a snug fit. While FIG. 5 illustrates the preferred configuration and arrangement of the second internal cavity, the second internal cavity contacting surface, and the second cover holes, it is contemplated within the scope of the invention that the second internal cavity, the second internal cavity contacting surface, and the second cover holes may be of any suitable configuration and arrangement. It is also contemplated within the scope of the invention that there may be more or fewer than four (4) second cover holes. More particularly, it is contemplated within the scope of the invention that there are no second cover holes.

Figure 6:
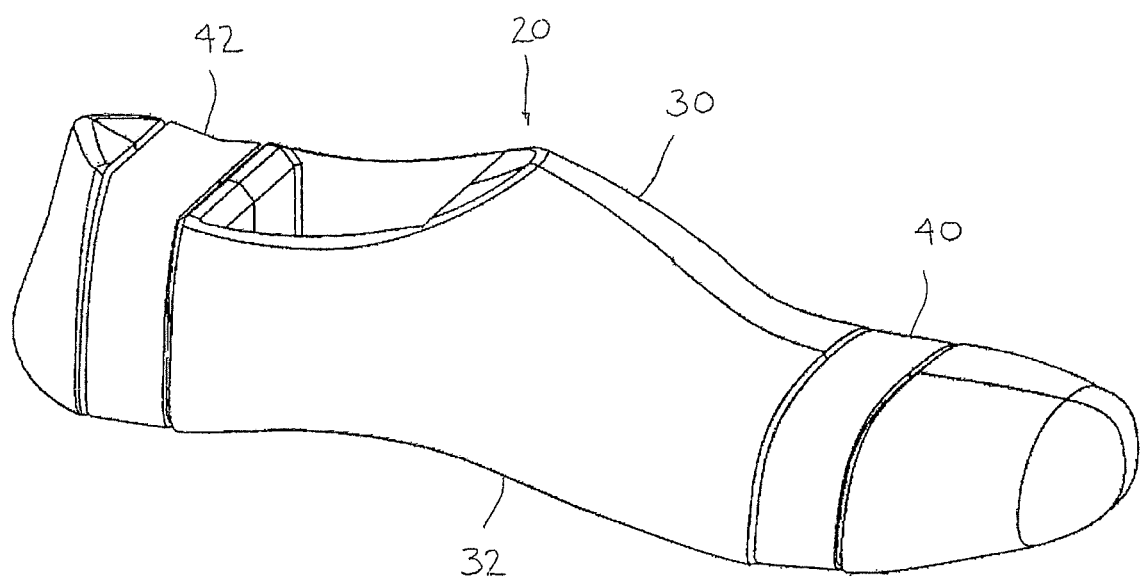
FIG. 6 is a front perspective view of the preferred prosthetic foot cover illustrated in FIGS. 1-5.

Referring now to FIG. 6, a front perspective view of preferred prosthetic foot cover 20 is illustrated. As shown in FIG. 6, preferred prosthetic foot cover 20 comprises first cover component 30, second cover component 32, and compression bands 40 and 42.

Figure 7:
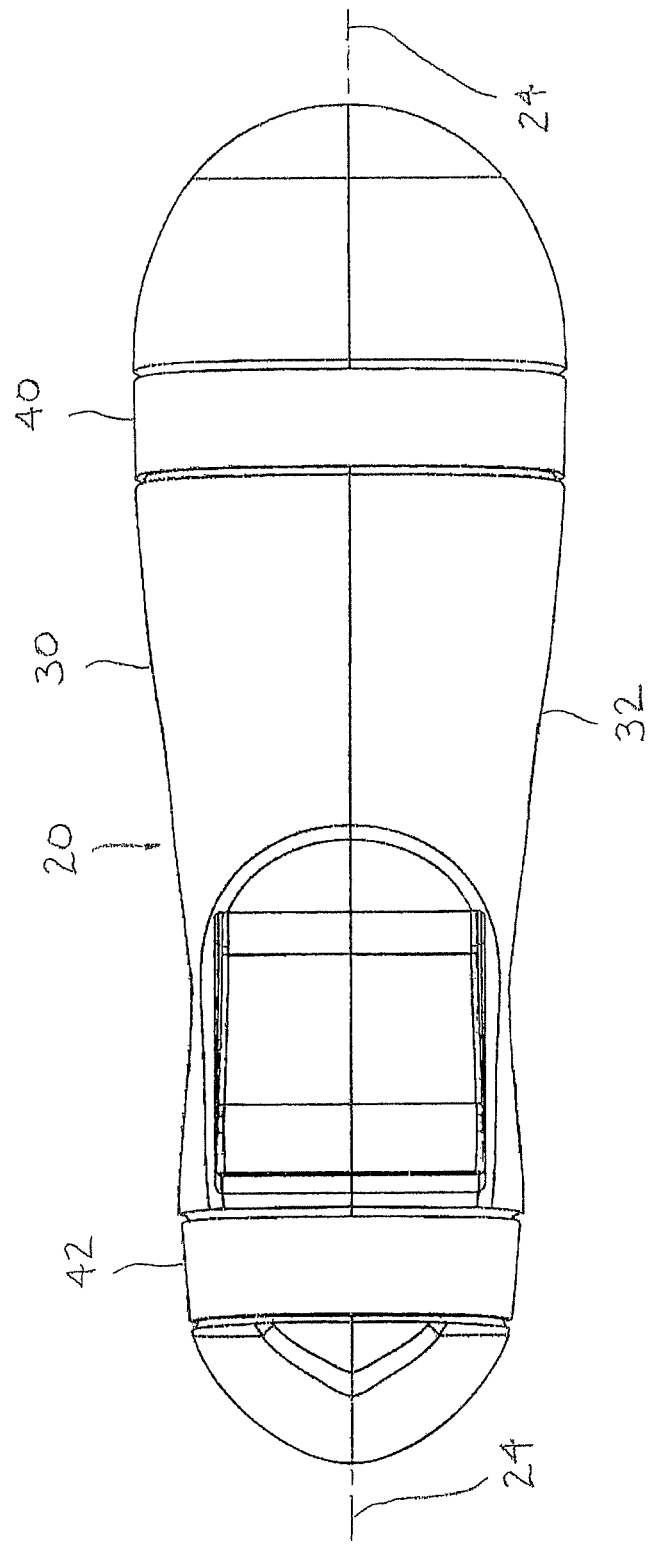
FIG. 7 is a top view of the preferred prosthetic foot cover illustrated in FIGS. 1-6.

Referring now to FIG. 7, a top view of preferred prosthetic foot cover 20 is illustrated. As shown in FIG. 7, preferred prosthetic foot cover 20 comprises first cover component 30, second cover component 32, and compression bands 40 and 42.

Figure 8:
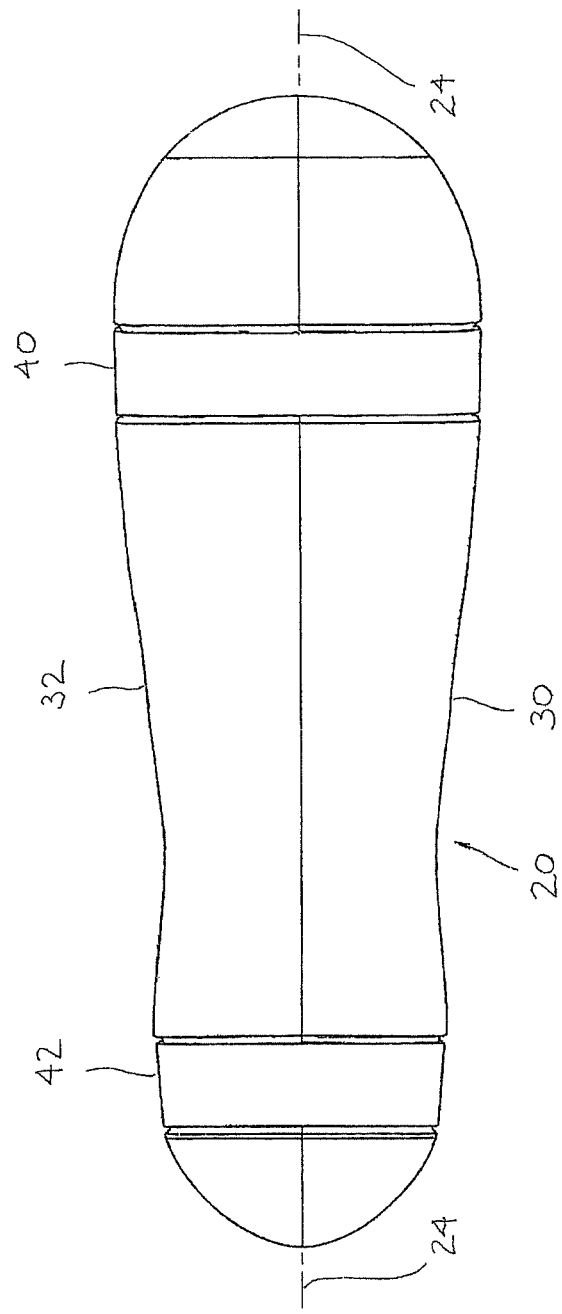
FIG. 8 is a bottom view of the preferred prosthetic foot cover illustrated in FIGS. 1-7.

Referring now to FIG. 8, a bottom view of preferred prosthetic foot cover 20 is illustrated. As shown in FIG. 8, preferred prosthetic foot cover 20 comprises first cover component 30, second cover component 32, and compression bands 40 and 42.

Figure 9:
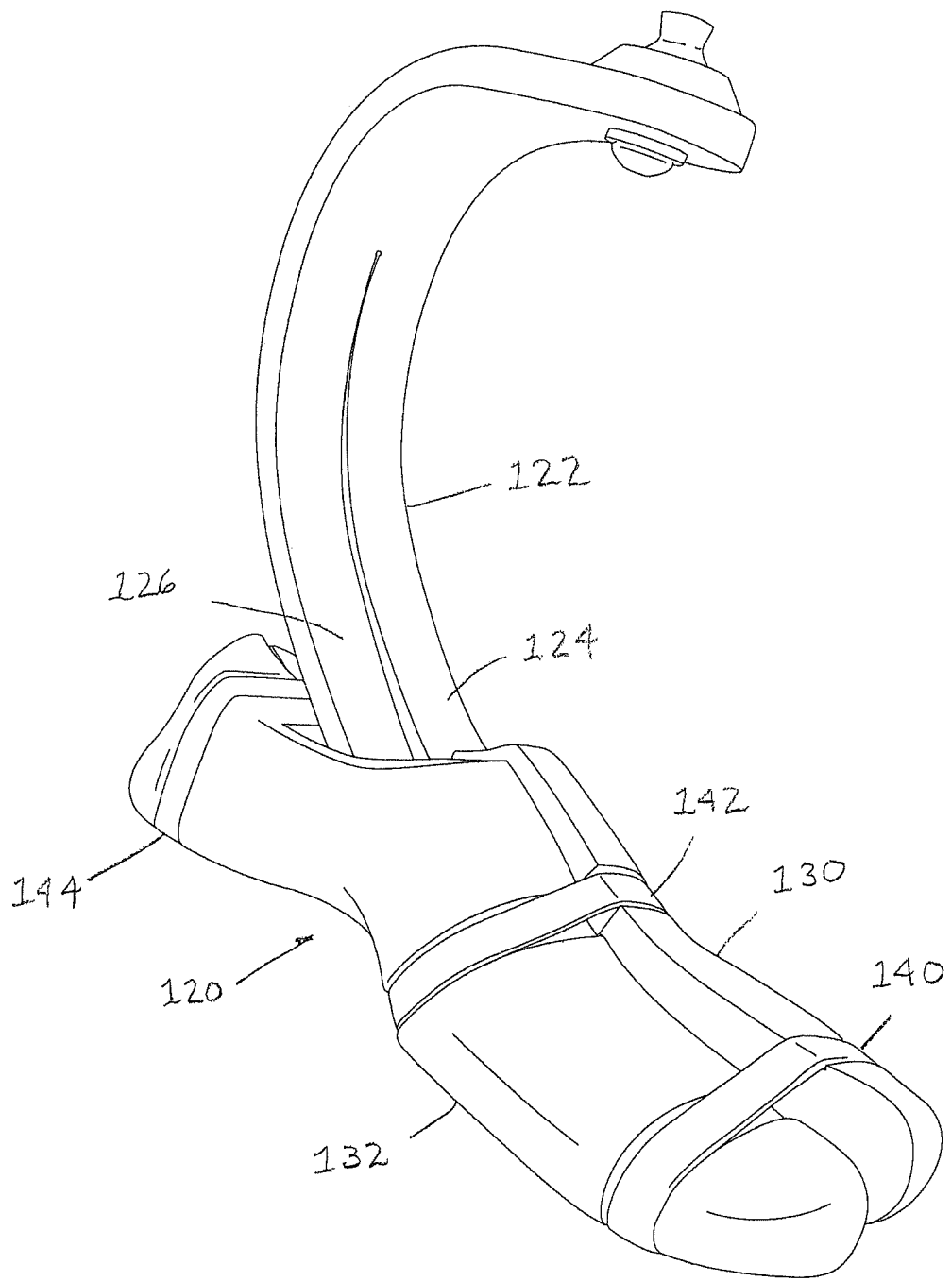
FIG. 9 is a front perspective view of a first alternative embodiment of the prosthetic foot cover in accordance with the present invention.

Referring now to FIG. 9, a front perspective view of a first alternative embodiment of the prosthetic foot cover in accordance with the present invention is illustrated. As shown in FIG. 9, the preferred prosthetic foot cover is designated generally by reference numeral 120. Preferred prosthetic foot cover 120 is illustrated with prosthetic foot 122 which has medial portion 124 and lateral portion 126. Preferred prosthetic foot cover 120 comprises first cover component 130, second cover component 132, first compression band 140, second compression band 142, and third compression band 144. Preferred prosthetic foot cover does not comprise any connectors like preferred prosthetic foot cover 20. As a result, first cover component 130 is capable of movement relative to second cover component 132 when medial portion 124 of prosthetic foot 122 moves relative to lateral portion 126 of the prosthetic foot. While FIG. 9 illustrates the preferred configuration and arrangement of the prosthetic foot cover, it is contemplated within the scope of the invention that the prosthetic foot cover may be of any suitable configuration and arrangement.

Figure 10:
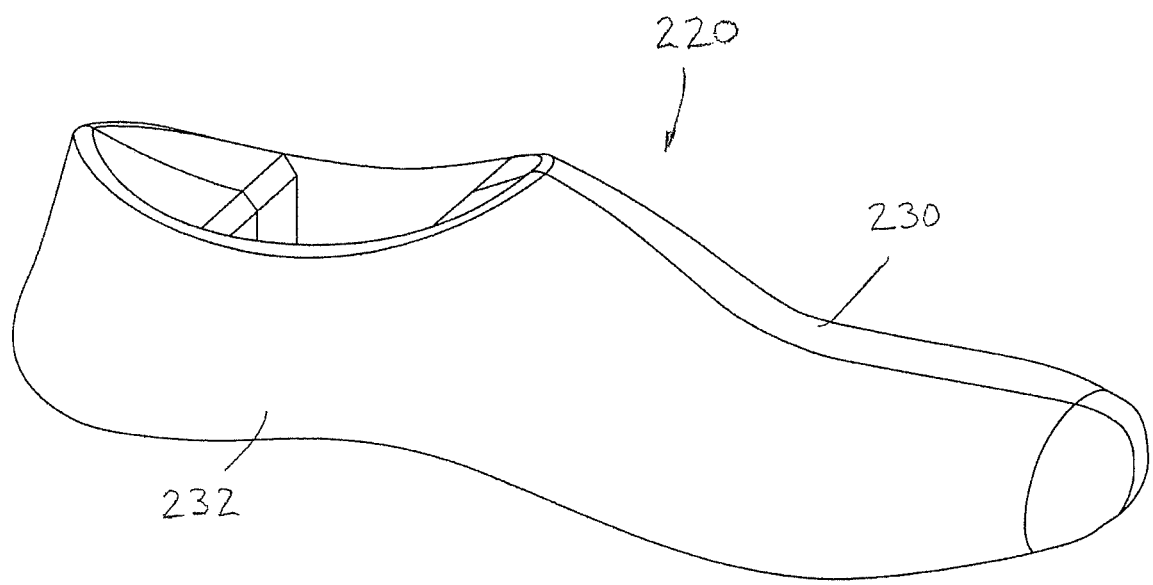
FIG. 10 is a front perspective view of a second alternative embodiment of the prosthetic foot cover in accordance with the present invention.

Referring now to FIG. 10, a front perspective view of a second alternative embodiment of the prosthetic foot cover in accordance with the present invention is illustrated. As shown in FIG. 10, the preferred prosthetic foot cover is designated generally by reference numeral 220. Preferred prosthetic foot cover 220 comprises first cover component 230 and second cover component 232. While FIG. 10 illustrates the preferred configuration and arrangement of the prosthetic foot cover, it is contemplated within the scope of the invention that the prosthetic foot cover may be of any suitable configuration and arrangement.

Figure 11:
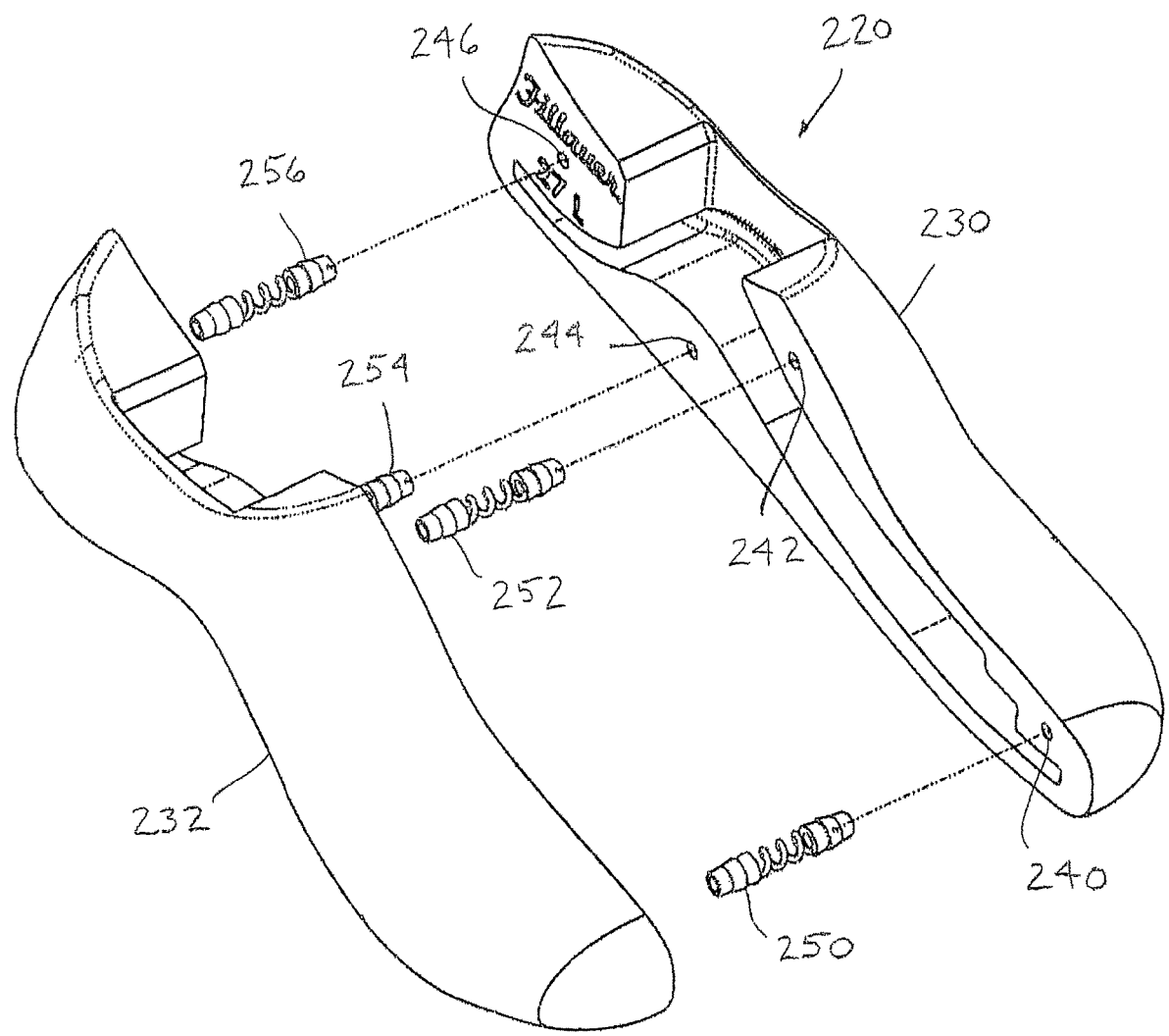
FIG. 11 is a front perspective exploded view of the second alternative embodiment of the prosthetic foot cover illustrated in FIG. 10.

Referring now to FIG. 11, a front perspective exploded view of preferred prosthetic foot cover 220 is illustrated. As shown in FIG. 11, preferred prosthetic foot cover 220 comprises first cover component 230 and second cover component 232. Preferred first cover component 230 comprises a plurality of holes 240, 242, 244, and 246 each of which is adapted to receive a portion of one of a plurality of flexible connectors 250, 252, 254, and 256. Preferred second cover 232 also comprises a plurality of corresponding holes adapted to receive a different portion of the plurality of flexible connectors 250, 252, 254, and 256. Preferred plurality of flexible connectors 250, 252, 254, and 256 permit preferred first cover component 230 to move relative to preferred second cover component 232. Preferred plurality of flexible connectors 250, 252, 254, and 256 may comprise springs, coils, barbs and the like.

Figure 12:
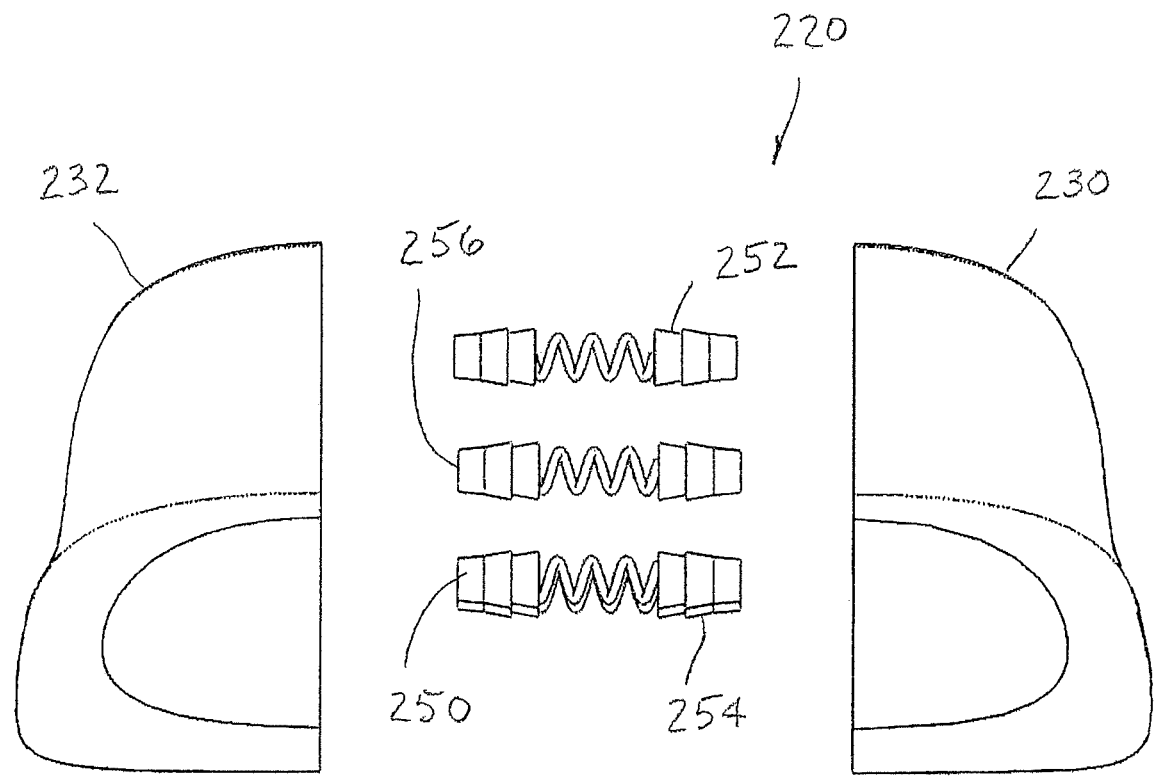
FIG. 12 is a front exploded view of the second alternative embodiment of the prosthetic foot cover illustrated in FIGS. 10 and 11.

Referring now to FIG. 12, a front exploded view of preferred prosthetic foot cover 220 is illustrated. As shown in FIG. 12, preferred prosthetic foot cover 220 comprises first cover component 230, second cover component 232, and plurality of flexible connectors 250, 252, 254, and 256.

Figure 13:
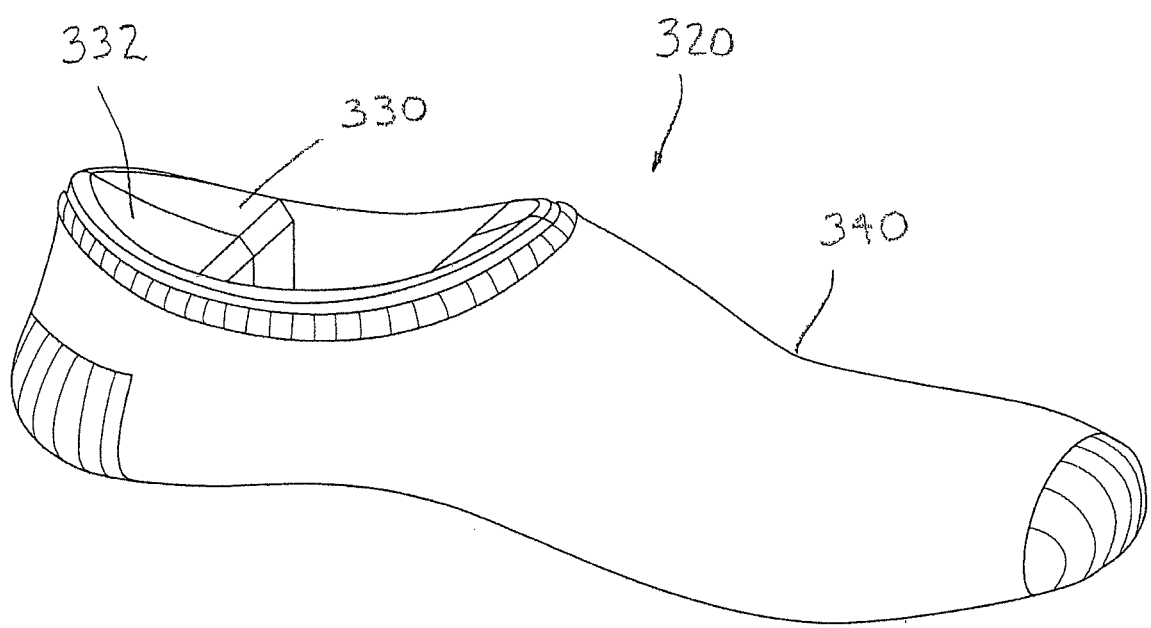
FIG. 13 is a front perspective view of a third alternative embodiment of the prosthetic foot cover in accordance with the present invention.

Referring to FIG. 13, a front perspective view of a third alternative embodiment of the prosthetic footcover in accordance with the present invention is illustrated. As shown in FIG. 13, the preferred third alternative embodiment of the prosthetic foot cover is designated generally by reference numeral 320. Preferred prosthetic foot cover 320 comprises first cover component 330, second cover component 332, and sock 340. Preferred sock 340 is a compression sock, but it is also contemplated within the scope of the invention that sock may be elastic mesh that allows multi-axial movement. While FIG. 13 illustrates the preferred configuration and arrangement of the prosthetic foot cover, it is contemplated within the scope of the invention that the prosthetic foot cover may be of any suitable configuration and arrangement.

Figure 14:
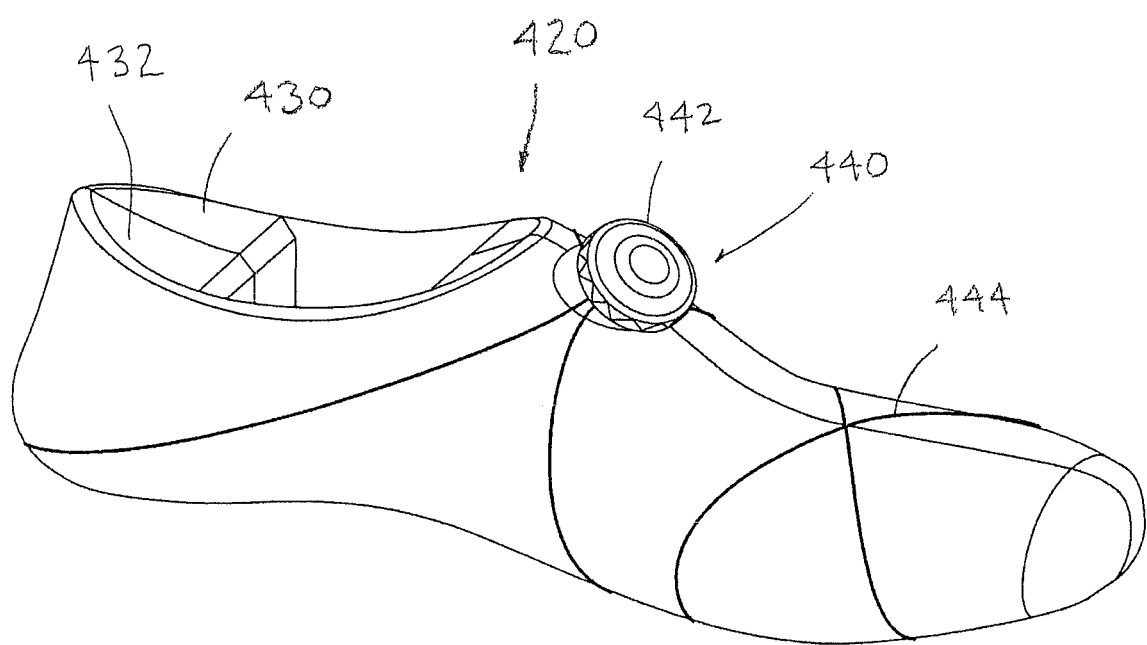
FIG. 14 is a front perspective view of a fourth alternative embodiment of the prosthetic foot cover in accordance with the present invention.

Referring now to FIG. 14, a front perspective view of a fourth alternative embodiment of the prosthetic foot cover in accordance with the present invention is illustrated. As shown in FIG. 14, the preferred fourth alternative embodiment of the prosthetic foot cover is designated generally by reference numeral 420. Preferred prosthetic foot cover 420 comprises first cover component 430, second cover component 432, and ratchet assembly 440. Preferred ratchet assembly comprises a BOA® fit system having micro-adjustable dial 442 and lace 444. While FIG. 14 illustrates the preferred configuration and arrangement of the prosthetic foot cover, it is contemplated within the scope of the invention that the prosthetic foot cover may be of any suitable configuration and arrangement.

Figure 15:
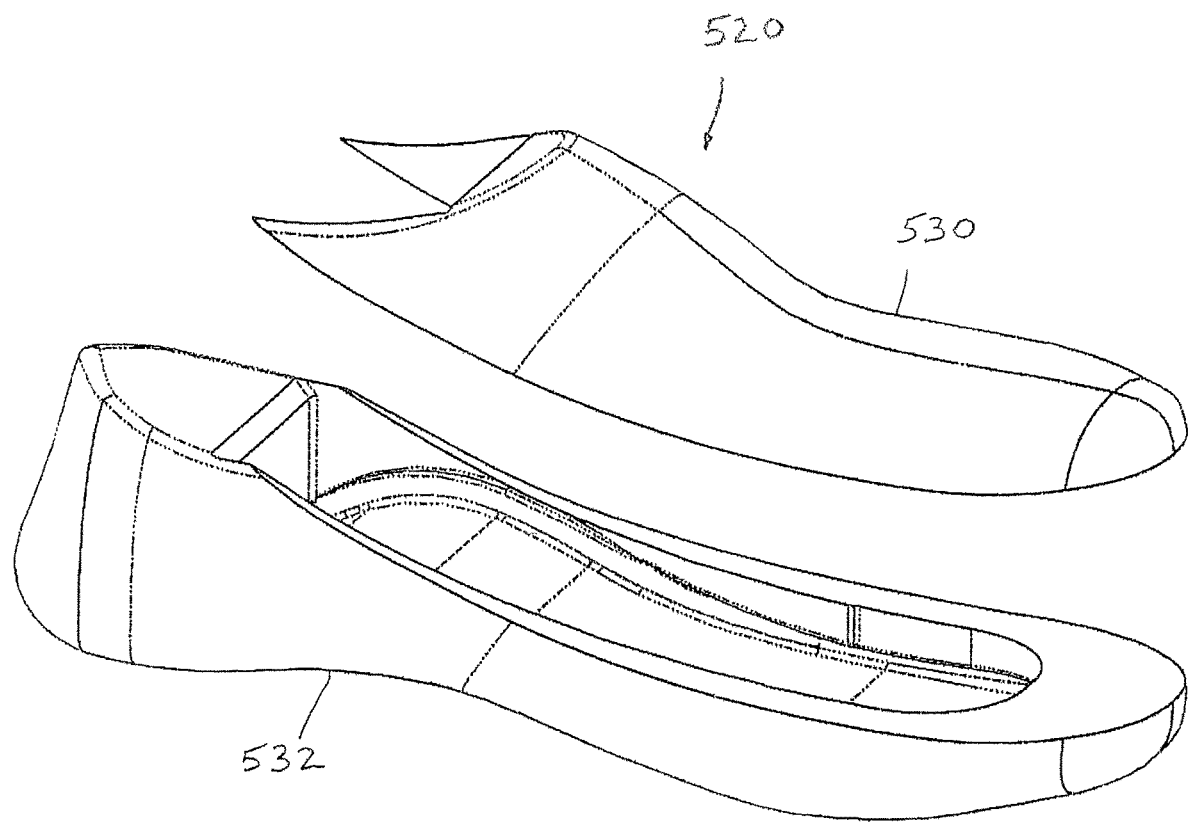
FIG. 15 is a front perspective exploded view of a fifth alternative embodiment of the prosthetic foot cover in accordance with the present invention.

Referring now to FIG. 15, a front perspective exploded view of a fifth alternative embodiment of the prosthetic foot cover in accordance with the present invention is illustrated. As shown in FIG. 15, the preferred fifth alternative embodiment of the prosthetic foot cover is designated generally by reference numeral 520. Preferred prosthetic foot cover 520 comprises first cover component 530 and second cover component 532. Preferred first cover component 530 is adapted to sit on top of preferred second cover component 532 and a prosthetic foot. Preferred second cover 532 is adapted to sit beneath preferred first cover component 530 and contact the plantar surface of a prosthetic foot. While FIG. 15 illustrates the preferred configuration and arrangement of the prosthetic foot cover, it is contemplated within the scope of the invention that the prosthetic foot cover may be of any suitable configuration and arrangement.

Figure 16:
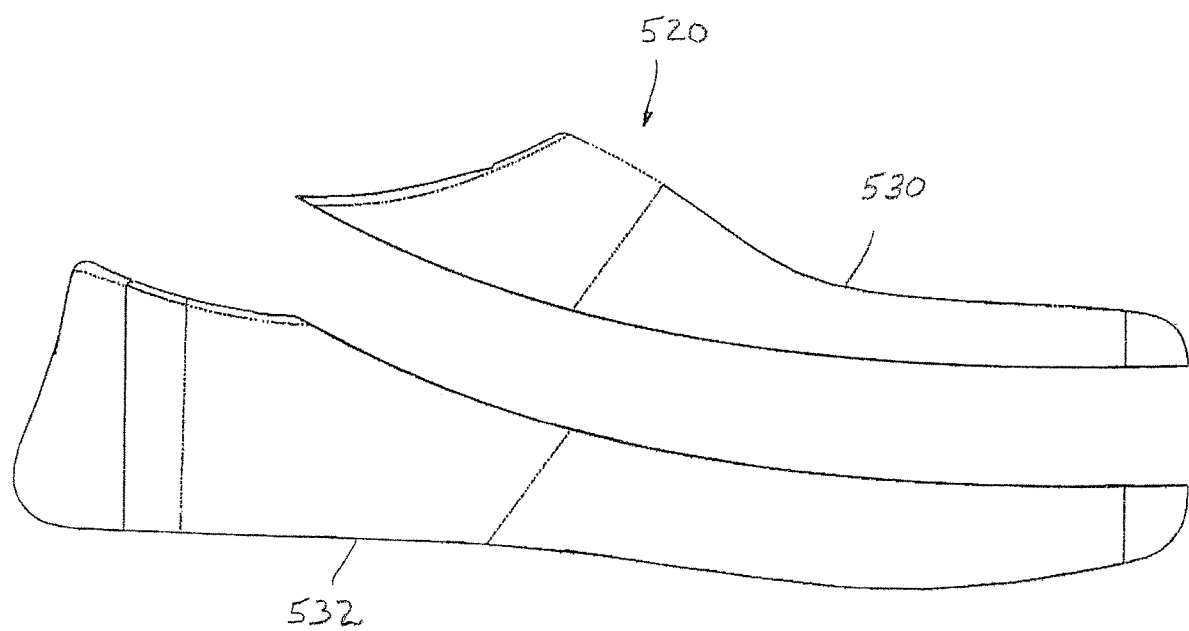
FIG. 16 is a right side exploded view of the preferred fifth alternative embodiment of the prosthetic foot cover illustrated in FIG. 15.

Referring now to FIG. 16, a right side exploded view of preferred prosthetic foot cover 520 is illustrated. As shown in FIG. 16, preferred prosthetic foot cover 520 comprises first cover component 530 and second cover component 532.

The invention also comprises a method for covering a prosthetic foot having a sagittal plane. The preferred method comprises providing a prosthetic foot cover as described and claimed herein. More particularly, the preferred prosthetic foot cover comprises a first cover component having a first internal cavity and being adapted to receive and cover a first portion of the prosthetic foot, a second cover component having a second internal cavity and being adapted to receive and cover a second portion of the prosthetic foot, and a means for detachably attaching the first cover component and the second cover component to the prosthetic foot. Preferably, the first internal cavity has a first internal cavity contacting surface that directly contacts the first portion of the prosthetic foot, and the second internal cavity has a second internal cavity contacting surface that directly contacts the second portion of the prosthetic foot. The preferred method also comprises installing the prosthetic foot cover on the prosthetic foot.

In other preferred embodiments of the method for covering a prosthetic foot, the method comprises removing the prosthetic foot cover from the prosthetic foot, installing the first cover component on the first portion of the prosthetic foot and installing the second cover component on the second portion of the prosthetic foot, removing the first cover component from the first portion of the prosthetic foot and removing the second cover component from the second portion of the prosthetic foot, and/or detachably attaching the first cover component and the second cover component to each other.

In operation, several advantages of the preferred embodiments of the prosthetic foot cover are achieved. For example, the preferred embodiments of the prosthetic foot cover do not inhibit movement of prosthetic feet and improve the functionality of prosthetic feet. More particularly, the preferred prosthetic foot covers do not restrict the traverse movement of prosthetic foot and improve the multi-axial performance of prosthetic feet. The preferred prosthetic foot covers are also easily customized so as provide support along the entire plantar surface of prosthetic feet and a smooth rollover and prevent movement of the foot covers relative to the feet. The preferred foot covers can also be customized for use with different types of shoes, such as flats and high heels, and eliminate the need for different feet for different types of shoes. The preferred foot covers can also be used without shoes and do not collect fluids or debris. The preferred foot covers are also adapted for use with a wide variety of devices, mechanisms, assemblies, and combinations thereof for easily installing them on and removing them from prosthetic feet. In addition, the preferred foot covers are durable and have a long lifespan. Still further, the preferred foot covers provide the user with sufficient feedback, unimpeded flexion, and energy return, and they do not tend to have a dampening effect that decreases the fidelity of the ground reaction forces experienced by the user.

Although this description contains many specifics, these should not be construed as limiting the scope of the invention but as merely providing illustrations of some of the presently preferred embodiments thereof, as well as the best mode contemplated by the inventors of carrying out the invention. The invention, as described herein, is susceptible to various modifications and adaptations, and the same are intended to be comprehended within the meaning and range of equivalents of the appended claims.

What is claimed is:

1. A prosthetic foot cover adapted for use on a prosthetic foot having a sagittal plane and a non-planar plantar surface, said prosthetic foot cover comprising:
    (a) a first cover component, said first cover component having a first internal cavity and being adapted to receive and cover a first portion of the prosthetic foot;
    (b) a second cover component, said second cover component having a second internal cavity and being adapted to receive and cover a second portion of the prosthetic foot;
    (c) a means for removably attaching the first cover component to the second cover component around the prosthetic foot;
    wherein the first internal cavity has a first internal cavity contacting surface that directly contacts substantially all of the non-planar plantar surface of the first portion of the prosthetic foot; and wherein the second internal cavity has a second internal cavity contacting surface that directly contacts substantially all of the non-planar plantar surface of the second portion of the prosthetic foot and wherein the first cover component and the second cover component are entirely discrete from each other; and wherein the foot cover is composed of a homogeneous linear spring rate material that produces a variable stiffness due to the substantially increasing/decreasing cross-sectional thickness along the length of the foot cover; and wherein the foot cover substantially encapsulates the volume of the lower prosthetic foot member providing substantial support around the contacting surfaces to allow uniform transition in ground reaction forces for smooth rollover and improved feedback.

2. The prosthetic foot cover of claim 1 wherein the first cover component and the second cover component are removably attached along the sagittal plane of the prosthetic foot.

3. The prosthetic foot cover of claim 1 wherein the foot cover supports the prosthetic foot along substantially the entire non-planar plantar surface.

4. The prosthetic foot cover of claim 1 wherein the first cover component and the second cover component comprise polyurethane.

5. The prosthetic foot cover of claim 1 wherein the first cover component and the second cover component comprise a cross-linking agent.

6. The prosthetic foot cover of claim 1 wherein the first cover component and the second cover component comprise ethylene-vinyl acetate.

7. The prosthetic foot cover of claim 1 wherein the first cover component and the second cover component comprise a thermoplastic elastomer.

8. The prosthetic foot cover of claim 1 wherein the means for removably attaching the first cover component to the second cover component comprises a hook and loop fastener.

9. The prosthetic foot cover of claim 1 wherein the means for removably attaching the first cover component to the second cover component comprises a compression band.

10. The prosthetic foot cover of claim 1 wherein the means for removably attaching the first cover component to the second cover component comprises a clip.

11. The prosthetic foot cover of claim 1 wherein the means for removably attaching the first cover component to the second cover component comprises a threaded fastener.

12. The prosthetic foot cover of claim 1 wherein the means for removably attaching the first cover component to the second cover component comprises a compression sock.

13. The prosthetic foot cover of claim 1 wherein the means for removably attaching the first cover component to the second cover component comprises a hole.

14. The prosthetic foot cover of claim 1 wherein the means for removably attaching the first cover component to the second cover component comprises a groove.

15. The prosthetic foot cover of claim 1 wherein the first internal cavity contacting surface of the first cover component does not move relative to the first portion of the prosthetic foot and the second internal cavity contacting surface of the second cover component does not move relative to the second portion of the prosthetic foot.

16. The prosthetic foot cover of claim 1 wherein the first internal cavity and the second internal cavity are configured to as to allow unimpeded flexion of the prosthetic foot energy storing element.

17. The prosthetic foot cover of claim 1 wherein the first cover component and the second cover component each have a bottom surface, and each of said bottom surfaces have a curvature that allows a smooth foot rollover.

18. A prosthetic foot cover adapted for use on a prosthetic foot having a sagittal plane and a plantar surface having an arch, said prosthetic foot cover comprising:
    (a) a first cover component, said first cover component having a first internal cavity, a plurality of first cover grooves, and a plurality of first cover holes, and said first cover component being adapted to receive and cover a first portion of the prosthetic foot;
    (b) a second cover component, said second cover component having a second internal cavity, a plurality of second cover grooves, and a plurality of second cover holes, and said second cover component being adapted to receive and cover a second portion of the prosthetic foot;

(c) a means for removably attaching the first cover component to the second cover component around the prosthetic foot;

wherein the first internal cavity has a first internal cavity contacting surface that directly contacts substantially all of the plantar surface of the first portion of the prosthetic foot including the arch; and wherein the second internal cavity has a second internal cavity contacting surface that directly contacts substantially all of the plantar surface of the second portion of the prosthetic foot including the arch; and wherein the first cover component and the second cover component are removably attached to each other along the sagittal plane of the prosthetic foot; and wherein the first cover component and the second cover component are entirely discrete from each other; and wherein the foot cover is composed of a homogeneous linear spring rate material that produces a variable stiffness due to the substantially increasing/decreasing cross-sectional thickness along the length of the foot cover; and wherein the foot cover substantially encapsulates the volume of the lower prosthetic foot member providing substantial support around the contacting surfaces to allow uniform transition in ground reaction forces for smooth rollover and improved feedback; and wherein the prosthetic foot cover provides support to the prosthetic foot along substantially the entire plantar surface including the arch.

19. A method for covering a prosthetic foot having a sagittal plane and a non-planar plantar surface, said method comprising:
  (a) providing a prosthetic foot cover, said prosthetic foot cover comprising:
    (i) a first cover component, said first cover component having a first internal cavity and being adapted to receive and cover a first portion of the prosthetic foot;
    (ii) a second cover component, said second cover component having a second internal cavity and being adapted to receive and cover a second portion of the prosthetic foot;
    (iii) a means for removably attaching the first cover component to the second cover component around the prosthetic foot;
    wherein the first internal cavity has a first internal cavity contacting surface that directly contacts substantially all of the non-planar plantar surface of the first portion of the prosthetic foot; and wherein the second internal cavity has a second internal cavity contacting surface that directly contacts substantially all of the non-planar plantar surface of the second portion of the prosthetic foot and wherein the first cover component and the second cover component are entirely discrete from each other; and wherein the foot cover is composed of a homogeneous linear spring rate material that produces a variable stiffness due to the substantially increasing/decreasing cross-sectional thickness along the length of the foot cover; and wherein the foot cover substantially encapsulates the volume of the lower prosthetic foot member providing substantial support around the contacting surfaces to allow uniform transition in ground reaction forces for smooth rollover and improved feedback;
  (b) installing the prosthetic foot cover on the prosthetic foot.

20. The method of claim 19 further comprising removing the prosthetic foot cover from the prosthetic foot.

21. The method of claim 19 further comprising installing the first cover component on the first portion of the prosthetic foot and installing the second cover component on the second portion of the prosthetic foot and removing the first cover component from the first portion of the prosthetic foot and removing the second cover component from the second portion of the prosthetic foot.

22. The method of claim 19 further comprising removably attaching the first cover component and the second cover component to each other.

\* \* \* \* \*